(12) United States Patent
Hohlbein

(10) Patent No.: US 7,007,332 B2
(45) Date of Patent: Mar. 7, 2006

(54) POWERED TOOTHBRUSH

(75) Inventor: Douglas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/079,325

(22) Filed: Mar. 14, 2005

(65) Prior Publication Data

US 2005/0155168 A1   Jul. 21, 2005

Related U.S. Application Data

(63) Continuation of application No. PCT/US03/28335, filed on Sep. 9, 2003.

(60) Provisional application No. 60/410,078, filed on Sep. 12, 2002.

(51) Int. Cl.
*A61C 17/34* (2006.01)

(52) U.S. Cl. .......................... 15/22.1; 15/22.2; 15/22.4

(58) Field of Classification Search ................. 15/22.1, 15/22.2, 22.4
See application file for complete search history.

(56) References Cited

U.S. PATENT DOCUMENTS

| 1,255,028 | A | | 1/1918 | Leonard et al. | |
|---|---|---|---|---|---|
| 1,657,229 | A | * | 1/1928 | Sferlazzo | ..................... 15/22.4 |
| 2,912,706 | A | | 11/1959 | Gerecke et al. | |
| 5,325,560 | A | | 7/1994 | Pavone et al. | |
| 5,625,916 | A | | 5/1997 | McDougall | |
| 5,784,743 | A | | 7/1998 | Shek | |
| 5,974,613 | A | | 11/1999 | Herzog | |
| 6,000,083 | A | * | 12/1999 | Blaustein et al. | ............... 15/28 |
| 6,314,606 | B1 | | 11/2001 | Hohlbein | |
| 6,347,425 | B1 | | 2/2002 | Fattori et al. | |
| 2003/0097723 | A1 | * | 5/2003 | Li | .............................. 15/22.1 |
| 2003/0140436 | A1 | | 7/2003 | Gatzemeyer et al. | |

* cited by examiner

*Primary Examiner*—Mark Spisich
(74) *Attorney, Agent, or Firm*—Harris A. Wolin

(57) ABSTRACT

A powered toothbrush is disclosed wherein portion of the toothbrush head is movable about a hinge. The movable portion of the head reciprocates about that hinge through the interaction of a flexible extension of that portion containing a slot. Movable within the slot is an offset end of a rotating drive shaft connected to the power source in the toothbrush. Translation of rotation movement of the drive shaft to reciprocating movement of the hinged head is achievable in a manner that the power source is not stalled or burned out if movement of the toothbrush head is prevented or limited.

7 Claims, 1 Drawing Sheet

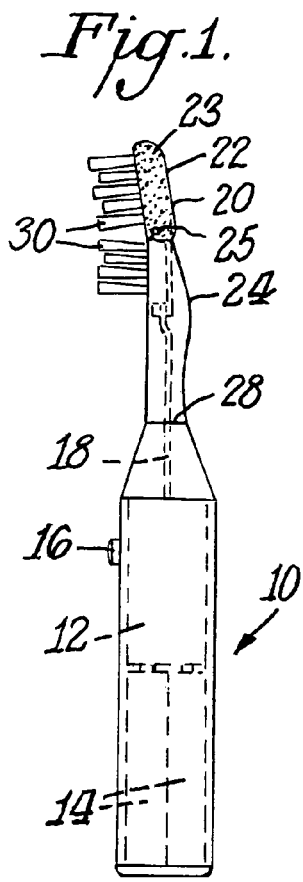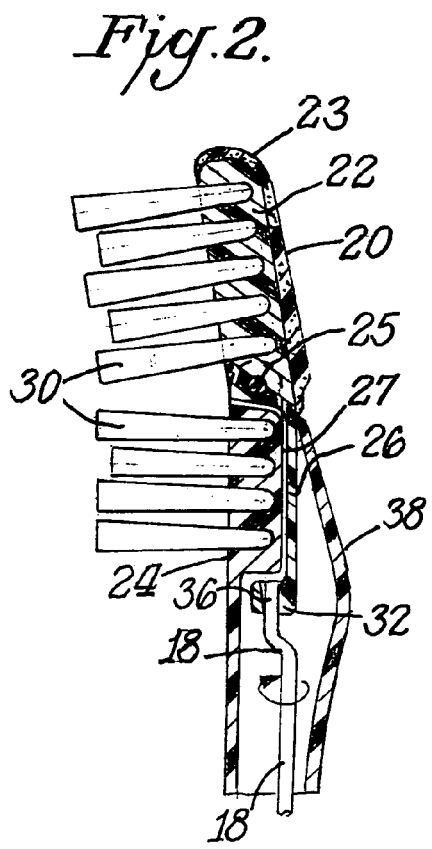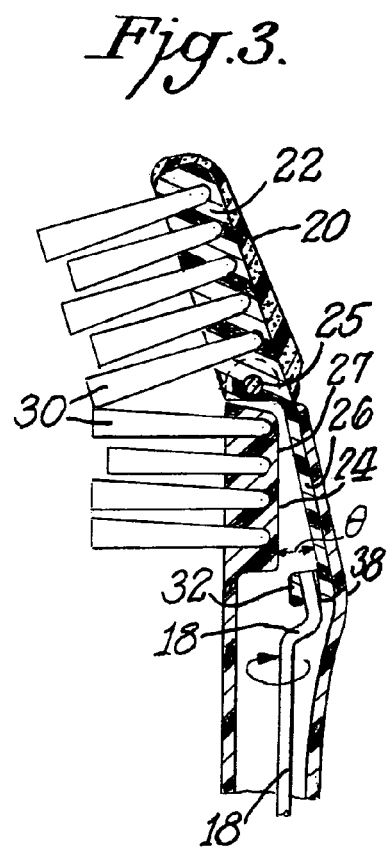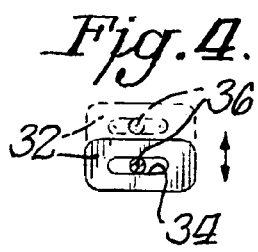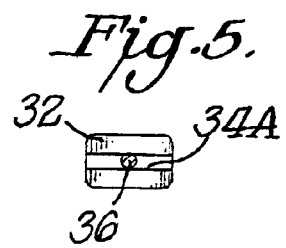

POWERED TOOTHBRUSH

This application is a continuation of application PCT/US2003/28335, filed Sep. 9, 2003, which claims the benefit of U.S. Provisional Application 60/410,078 filed Sep. 12, 2002, both of which are incorporated herein by reference in their entirety.

BACKGROUND OF THE INVENTION

As toothbrush design has evolved in an effort to improve cleaning of teeth and gums, the complexity of toothbrushes and their functions have increased. Powered toothbrushes are one example of efforts to improve tooth cleaning by including one or more movable sets of cleaning elements. Another approach to improving cleansing of teeth is use of a toothbrush head that is articulated or segmented to better follow the rounded curvature of teeth aligned in the human jaw.

However, little has been done to synergistically combine these approaches in a manner that achieves effective cleaning of all teeth while carefully avoiding harm to the gum line. That is an object of this invention.

One approach to a segmented or articulated toothbrush head is shown in U.S. Pat. No. 6,314,606B1 issued Nov. 13, 2001 to Douglas Hohlbein. This patent disclosed a two part toothbrush head joined by a living hinge or other integrally molded elastomeric-type connector. Under one embodiment of this patent, the part of the toothbrush head most remote from the handle is normally angled with respect to the head section nearest the handle. According to the patent, the flexible angulation of the head accommodates to the curvature of the human jaw, as well as the relatively straight portions of the jaw. In addition, the flexibility of at least a portion of the head provides a more gentle treatment of the gum line because the force applied by the user is moderated and more evenly distributed through the hinge (column 1, lines 61–67).

SUMMARY OF THE INVENTION

A powered toothbrush is disclosed which drives a moving portion of the toothbrush head in a reciprocal motion about a hinge joining the moving portion of the head to a fixed portion of the head. The reciprocation movement provides a power assisted tip pulsing action.

To facilitate this movement, the living hinge construction used in the aforementioned patent may be replaced with a less rigid hinge such as a pivoting pin and socket joint. However, the hinge construction may be of any type that does not affect the powered reciprocating of the moving portion of the toothbrush head.

The movable section of the toothbrush head can be powered by using the type of drive mechanism shown in U.S. Pat. No. 5,625,916.

Another powered toothbrush is described in U.S. Pat. No. 6,347,425B1 issued Feb. 19, 2002 and assigned to the assignee of this invention. It discloses an electrically powered toothbrush having rotatable drive shaft with an end off-set from the central longitudinal axis of the drive shaft which provides a reciprocating, rocking motion to a set of cleaning elements.

In a preferred embodiment, the movable portion of the toothbrush head has a flange extending therefrom toward the handle. This flange preferably has a horizontal slot that accepts an offset in a drive shaft extending from the motive source in the toothbrush handle for example, a motor. This offset in the drive shaft is similar to that shown in U.S. Pat. No. 6,347,425B1 discussed above.

The slot in the flange interacts with the offset in the drive shaft to form a "slip clutch" so that if an excessive load is applied to the movable portion of the toothbrush head, the motor powering the toothbrush will not stall. This "slip clutch" effect also has the advantage of being a safety mechanism when in use. More particularly, the slip clutch limits operation of the movable portion of the head if the user applies excessive force to the handle.

The use of the flange extending from the powered portion of the toothbrush head also permits a low profile of the toothbrush head. That low, compact profile facilitates insertion and use of the toothbrush in the human mouth.

BRIEF DESCRIPTION OF THE DRAWINGS

This invention is capable of use in a broad array of consumer packaging and products. The drawings illustrate one use of the invention and are not to be construed as the only embodiment of the invention.

FIG. 1 is a perspective view of a power toothbrush with a power driven movable portion of a toothbrush head.

FIG. 2 is an enlarged cross-sectional view showing the movable portion of the toothbrush head with attached flange powered by an offset drive mechanism, in one position.

FIG. 3 is an enlarged cross-sectional view showing the movable portion of the toothbrush in another position.

FIG. 4 is an elevational view showing the slot in a tab on the flange attached to the movable portion of the toothbrush head in alternate positions.

FIG. 5 is an elevational view showing an alternate design of the slot on the tab attached to the movable portion of the toothbrush head.

DETAILED DESCRIPTION OF THE PREFERRED EMBODIMENT

The powered toothbrush 10 of this invention includes a motor 12 powered by batteries or rechargeable energy source 14. The toothbrush 10 can be operated by depressing or other-wise operating power switch 16 on the body of toothbrush 10.

A powered motor 12 rotates in a conventional manner. A drive shaft 18 is connected to the motor 12 through a shaft coupling or other means of directly transferring the motor's rotation to drive shaft 18.

Toothbrush 10 contains a two part articulated head 20 comprising a movable portion 22 and stationary portion 24 formed as part of the overall powered toothbrush. Movable portion 22 preferably has a soft elastomeric coating 23 which reduces the impact thereof on the users teeth and mouth during use. These portions of head 20 are preferably joined by a hinge 25 that allows movable portion 22 to freely move relative to portion 24. It is envisioned that the portion of toothbrush 10 containing the head 20 could be adapted for replacement by inserting a new head into the powered portion of the toothbrush at or about the location indicated by reference numeral 28.

The stationary 24 and movable 22 portions of the toothbrush head 20 contain cleaning elements 30. Cleaning elements 30 are arranged in both portions of head 20 in a known manner. Any suitable form of cleaning elements may be used as the cleaning elements 30 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions. Where bristles are used, the bristles could be mounted to tuft blocks or sections by extending through suitable openings in the tuft blocks so that the base of the bristles is mounted within or below the tuft block.

It is to be understood that the specific illustration of the cleaning elements is merely for exemplary purposes. The invention can be practiced with various combinations (such as stapled or in-mold technology bristles, etc.) and/or with the same bristle or cleaning element materials (such as nylon bristles, spiral bristles, rubber bristles, etc.) Similarly, while the Figures illustrate the cleaning elements to be generally perpendicular to head 20, some or all of the cleaning elements may be angled at various angles with respect to the surface of head 20. It is thereby possible to select the combination of cleaning element configurations, materials and orientations to achieve specific intended results to deliver additional oral health benefits, like enhanced cleaning, tooth polishing, tooth whitening and/or massaging of the gums.

The changes in orientation of movable portion 22 during operation are best understood by comparing FIGS. 2 and 3. Movable portion 22 has a flange 26 attached thereto extending from the area of movable portion 22 adjacent the last row of cleaning elements and extending lengthwise toward the drive shaft 18. This flange 26 may be molded as part of movable portion 22 or affixed thereto. The flange 26 terminates at a tab 32 which is preferably aligned approximately perpendicular to the axis of drive shaft 18.

Tab 32 at the end of flange 26 contains a slot 34 for receipt of an offset end 36 or elbow of drive shaft 18 (See FIGS. 2 and 4). As drive shaft 18 rotates unidirectionally under motor power the offset end 36 of the shaft 18 engages the side edges of slot 34. This causes the flange 26 to rotate counterclockwise around hinge 25 from a position immediately adjacent the back side 27 of the stationary portion 24 of head 20 (FIG. 2) to a position 15–30 degrees (angle θ) from that position 6 (FIG. 3). As the drive shaft rotates, typically at several hundred revolutions per minute, movable portion 22 of head 20 rapidly moves about hinge 25 resulting in a vigorous passage of cleaning elements 30 over the user's teeth and gums. This rapid movement helps to clean the user's teeth and stimulate the user's gums.

FIGS. 4 and 5 illustrate alternative configurations 34 and 34A for slot 34. Slot 34 of FIG. 4 is closed at both ends to contain the offset end 36 of shaft 18 whereas slot 34A shown in FIG. 5 allows movement of offset end 36 across the entire width of tab 32 attached to flange 26.

Flange 26 is preferably formed of a moderately flexible material that permits its movement independent of movable portion 22 of the toothbrush head 20. Thus, if the user applies considerable force on the end of movable portion 22, that tends to keep it in the position shown in FIG. 4 while drive shaft 18 is turning, the flexibility of flange 26 will allow the motor to continue turning even though the movable portion 22 of head 20 is not moving or only slightly moving. This flexibility in flange 26, coupled with the slot 34 or 34A in tab 32, prevents stalling of motor 12 in those situations where unusual pressure is exerted on the movable portion 22 of head 20.

Under normal operation tab 32 will be displaced in a plane perpendicular to the axis of the toothbrush, and the drive shaft 18, as the offset end 36 of that shaft rotates with the shaft. The amount of movement of tab 32, and consequent movement of movable portion 22 can be regulated by the distance between the axis of drive shaft 18 and the offset end 36 of that shaft. FIG. 4 illustrates this movement as the drive shaft 18 moves to opposite extremes of rotation. The full lines in FIG. 4 represent the placement of tab 32 when movable portion 22 of head 20 is in the position shown in FIG. 2. The phantom lines correspond to its position when movable portion 22 is in the FIG. 3 position.

To improve the cleansing of toothbrush 10 and preserve the operating parts 18, 26 and 32 from corrosion and or contamination, a cover 38 is placed over these parts. The cover 38 is preferably flexible or molded to allow free movement of flange 26 under power of drive shaft 18.

What is claimed is:

1. A powered toothbrush comprising a power source and a toothbrush head, said toothbrush head having a stationary portion and a movable portion each having cleaning elements extending therefrom, a rotatable drive shaft operatively connected to the power source, the drive shaft having an offset end engaged in a slot adjacent one end of a flexible flange connected to the movable portion of the toothbrush head, whereby the movable portion of the toothbrush head reciprocates about an axis that is lateral to the longitudinal axis of the toothbrush head across a front face of the toothbrush head as the offset end of the drive shaft travels in the slot.

2. The powered toothbrush of claim 1 wherein the movable portion of the toothbrush head is hinged to the stationary portion of the toothbrush head.

3. The powered toothbrush of claim 2 wherein the movable portion of the toothbrush head is flexibly connected to the stationary portion of the toothbrush head.

4. The powered toothbrush of claim 1 wherein the movable portion of the toothbrush head includes a soft elastomeric coating.

5. The powered toothbrush of claim 1 wherein a cover overlays the drive shaft and flexible flange.

6. The powered toothbrush of claim 5 wherein the cover is made of a flexible material.

7. The powered toothbrush of claim 5 wherein the cover is molded in a shape which permits free movement of the drive shaft and flexible flange therein.

* * * * *